United States Patent [19]

Pena

[11] 4,029,095

[45] June 14, 1977

[54] DEVICE FOR CIRCULATING TREATING FLUID THROUGH THE NASAL FOSSAE

[76] Inventor: Jose Baya Pena, Paseo Generalisimo 98, Masnou (Barcelona), Spain

[22] Filed: Jan. 9, 1976

[21] Appl. No.: 647,788

[30] Foreign Application Priority Data

Jan. 10, 1975 Spain ........ 208987

[52] U.S. Cl. ........ 128/250

[51] Int. Cl.² ........ A61M 7/00

[58] Field of Search ........ 128/250, 248, 230, 231, 128/232

[56] References Cited

UNITED STATES PATENTS

| | | | |
|---|---|---|---|
| 128,257 | 6/1872 | Snyder | 128/250 X |
| 1,487,252 | 3/1924 | Lore | 128/250 |
| 1,502,163 | 7/1924 | Sprague | 128/250 |
| 1,603,758 | 10/1926 | Fisher | 128/250 |
| 2,078,180 | 4/1937 | Kronenberg | 128/250 X |

*Primary Examiner*—John D. Yasko

*Attorney, Agent, or Firm*—Steinberg & Blake

[57] ABSTRACT

A device for circulating treating fluid through the nasal fossae includes a pump which has a suction inlet and a pressure outlet. A pair of elongated tubular structures respectively communicate with the suction inlet and pressure outlet, and these tubular structures have distant from the pump end portions respectively adapted to be placed in communication with the nasal fossae. A suitable treating fluid is adapted to be situated in one of the tubular structures so that when the pump is operated the treating fluid will be circulated from the pressure outlet of the pump through the tubular structure connected thereto into one of the nasal fossa and returned through the other nasal fossa into the other tubular structure to be sucked through the latter back to the suction inlet of the pump so that in this way a suitable treating fluid can be circulated through the nasal fossae.

10 Claims, 3 Drawing Figures

DEVICE FOR CIRCULATING TREATING FLUID THROUGH THE NASAL FOSSAE

BACKGROUND OF THE INVENTION

The present invention relates to devices for treating the nasal fossae.

As is well known, the nasal passages are at times greatly inconvenienced by increases in secretion of nasal mucosa, creating considerable discomfort to the individual while at the same time providing a possible center of infection which may spread and ultimately have a serious effect on the individual.

Up to the present time there has been no efficient device for cleaning and disinfecting the nasal fossae. There are known drugs adapted for local application in the form of simple aerosols or sprays. Devices of this type succeed in introducing a medication, for example, into the nasal fossae, but they are not capable of extracting mucous which accumulates in the deepest regions of the nasal fossae.

SUMMARY OF THE INVENTION

It is accordingly a primary object of the present invention to provide a device which will solve the above problems.

In particular, it is an object of the present invention to provide a relatively simple device which can very efficiently treat the nasal fossae with a suitable treating fluid which will serve for cleaning and/or disinfecting the nasal fossae.

Also, it is an object of the present invention to provide a device of this type which can conveniently be operated by the individual, so that professional services are not required.

Furthermore, it is an object of the present invention to provide a device of this type which is relatively inexpensive and convenient to use in an effective manner by an untrained individual.

According to the invention the device includes a pump means having a suction inlet and a pressure outlet. A suction tubular means communicates with the suction inlet while a pressure tubular means communicates with the pressure outlet of the pump means. These tubular means respectively have end portions distant from the pump means and provided respectively with means for placing the interiors of the tubular means respectively in communication with the nasal fossae. Thus, when a suitable treating fluid is situated in one of the tubular means the pump means can be operated for delivering the treating fluid under pressure through the pressure tubular means into one nasal fossae with the treating fluid than flowing to the other nasal fossae to be withdrawn from the latter into the suction tubular means back to the suction inlet of the pump means from where the fluid is again circulated. The end portions of the suction and pressure tubular means may be provided with cannulas for introduction into the nose openings to place the interiors of the tubular means in communication with the nasal fossae. A part of the suction tubular means takes the form of a container means which is adapted to contain the treating fluid in the form of a liquid of a disinfectant nature or also possibly of a medicating nature. The pump means permits the establishment of a closed circulating path of the treating fluid which enters through one of the nose openings and after passing through the nasal fossae is expelled back to the container means through the other nose opening, with the device preferably including a purifying filter which cleans the extracted liquid before returning it to the first nasal cavity through the pressure tubular means. In addition, the device is preferably provided with a pressure-limiting means for compensating for any tendency to create an undesirable overpressure.

This latter pressure-limiting means for compensating overpressure may be formed by a portion of the pressure tubular means which is made of an elastic deformable wall capable of expanding in response to excessive pressure so as to prevent the buildup of excessive pressure.

The pump means may be a motor-driven pump unit, preferably driven by way of a suitable micromotor. However, the pump means can also be a manually operable pump means in the form of an elastic bulb capable of being manually compressed, and capable of expanding when released by the operator, this particular pump means having at its suction inlet and pressure outlet, respectively, a pair of one-way valves which permit the fluid to flow only from the suction tubular means into the elastic bulb when the latter expands and from the elastic bulb only into the pressure tubular means when the elastic bulb is compressed by the operator.

The ends of the pair of tubular means which are distant from the pump means are preferably equipped with cannulas respectively having at their exteriors elastic flange-like lips projecting radially from the cannulas and adapted to provide a substantially fluid-tight fit for the pair of tubular means at the nasal fossae.

BRIEF DESCRIPTION OF DRAWINGS

The invention is illustrated by way of example in the accompanying drawings which form part of this application and in which.

DESCRIPTION OF PREFERRED EMBODIMENTS

Figure 1:
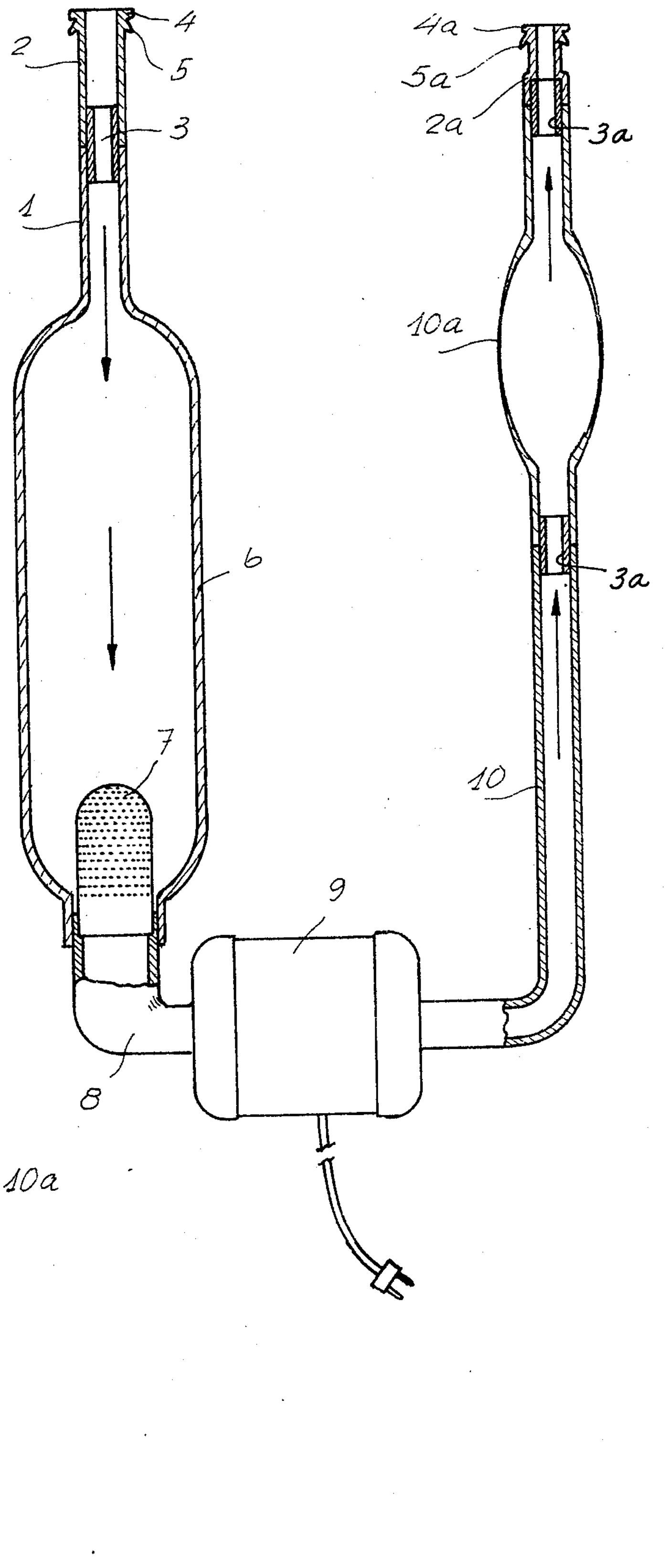
FIG. 1 is a partly sectional elevation of one possible embodiment of a device according to the invention.

Referring now to the drawings, the device shown in FIG. 1, which may be used for cleaning and/or disinfecting the nasal fossae, includes a pump means 9 in the form of a well known small pump driven by an electric micromotor which forms an integral part of the unit which forms the pump means 9. Such units are well known. The pump means 9 has at its right end, as viewed in FIG. 1, a pressure outlet and at its left end, as viewed in FIG. 1, a suction inlet.

A suction tubular means communicates with the suction inlet of the pump means 9. This suction tubular means includes a tubular portion 8 in the form of a suitable elbow situated directly at and communicating with the suction inlet of the pump means 9. This portion 8 of the suction tubular means communicates fluid-tightly at its end distant from the pump means 9 with an elongated container means 6 which forms part of the suction tubular means and which is adapted to contain in a suitable treating fluid. It will be noted that the diameter of the container means 6 of the suction tubular means is greater than that of the elbow portion 8 of the suction tubular means. At its upper end, as viewed in FIG. 1, the container means 6 communicates with an elongated portion 1 of the suction tubular means which again is of a smaller diameter than the container means 6. At its end portion distant from the pump means 9 the suction tubular means is provided with a means for placing the interior of the suction tubular means in communication with a nasal fossa. For this purpose the tubular portion 1 of the suction tubular means is connected with a cannula 2 terminating at its free end in a flange 4 behind which is situated a flexible elastic flange-like lip 5 which tapers to a relatively sharp edge, as illustrated, and which is adapted to make a substantially flulid-tight engagement with a nasal fossa. Thus, at least the lip 5 is made of an elastic material, although the remainder of the cannula 2 and the tubular portion 1, the container means 6, and the elbow 8 also may be made of an elastic and flexible tubular material. However, in order to connect the cannula 2 to the tubular portion 1 a rigid sleeve 3 is situated within the cannula 2 and the tubular portion 1 bridging the ends of the parts 1 and 2 which butt against each other and extends beyond these ends partly into the tubular portion 1 and partly into the cannula 2, as illustrated. Thus, all of the above structure connected to the suction inlet of the pump means 9 forms the equivalent of a continuous unitary tubular structure which at the cannula 2 is adapted to be placed in substantially fluid-tight communication with a nasal fossa.

As a further feature of the invention, however, a filter means 7 is situated between the container means 6 and the suction inlet of the pump means 9. In the illustrated example the filter means 7 takes the form of a hollow cup member having a bottom open end and an upper hemispherical end, this member being formed with a multiplicity of perforations through which the treating fluid can pass while the perforations are small enough to filter from the fluid which reaches the suction inlet any solid particles or the like which are withdrawn from the nasal fossae and which should not be recirculated. Thus, the filter 7 has substantially the configuration of an inverted test tube or thimble provided with a multiplicity of filtering perforations as illustrated.

The pressure outlet of the pump means 9 is connected to and communicates with a pressure tubular means including the elongated flexible tubular portion 10 connected by a rigid sleeve 3*a*with an elongated tubular portion 10*a*the wall of which is made of an elastic deformable material capable of expanding in response to excessive pressure so as to form a pressure-limiting means. The upper end of this portion 10*a*of the pressure tubular means is connected by a second substantially rigid sleeve 3*a* with a second cannula 2*a*which is substantially identical with the cannula 2, although being somewhat shorter than the latter, this cannula 2*a*being provided with an end flange 4*a*as well as with a flexible elastic sealing lip 5*a* situated behind the flange 4*a* and having substantially the same construction as the lip 5 described above.

Figure 3:
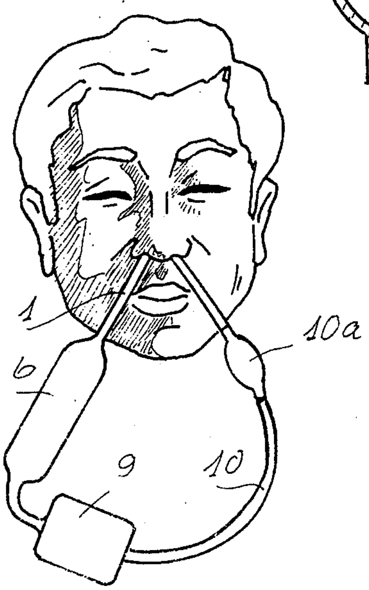
FIG. 3 illustrates how the device of the invention is used.

The above-described structure is used in the manner illustrated in FIG. 3. Thus FIG. 3 illustrates how the pair of tubular means are respectively inserted through the nostrils sufficiently to place the cannulas 2 and 2*a*respectively in substantially fluid-tight communication with the nasal fossae by way of the elastic flange-like elements 5 and 5*a*. However, prior to introduction of the pair of tubular means into the nostrils, a suitable treating fluid is situated in the container means 6 which forms part of the suction tubular means. This treating fluid can simply be dropped into the container means 6 through the upper open end of the cannula 2. For this purpose the treating fluid can take the form of suitable disinfecting liquid or a liquid which has therapeutic properties, or, of course, a liquid which is both disinfecting as well as therapeutic. For example, the treating fluid may take the form of a suitable saline solution. However, it is possible also to use a suitable decongestant such as phenylephrine hydrochloride. The pump means 9 is adapted to have its electric micromotor connected to a suitable source of energy by way of the cord and plug schematically shown at the lower part of FIG. 1. If desired a suitable switch may be available to turn the motor on and off. Thus, with the treating liquid situated in the container means 6 and the pair of tubular means respectively communicating with the nasal fossae as illustrated in FIG. 3, the pump means may be operated to suck the treating fluid from the container means 6 through the filter 7 and the elbow 8 into the suction inlet of the pump means 9 with this fluid then being delivered under pressure to the pressure tubular means through the tube 10 thereof and then through the pressure-limiting means 10*a*thereof into one nasal fossae through the cannula 2*a*,with a substantially fluid-tight connection being provided at this location by the lip 5*a*. This treating fluid will circulate through the nasal fossae to again be sucked back into the container means 6 through the cannula 2, the filter 7 serving to prevent matter such as collected mucous and the like from being carried through the pump means 9 back to the pressure tubular means. Thus the treating liquid is circulated through the nasal fossae, carrying along accumulated mucous with impurities being filtered by the filtering means 7. It will be noted that through this device a closed circuit is formed. If pressure should tend to build up to an undesirable level the elastic wall portion 10*a* will expand to increase the volume at the portion of the pressure tubular means where the elastic wall portion 10*a* is situated so as to prevent in this way creation of an excessive pressure.

Figure 2:
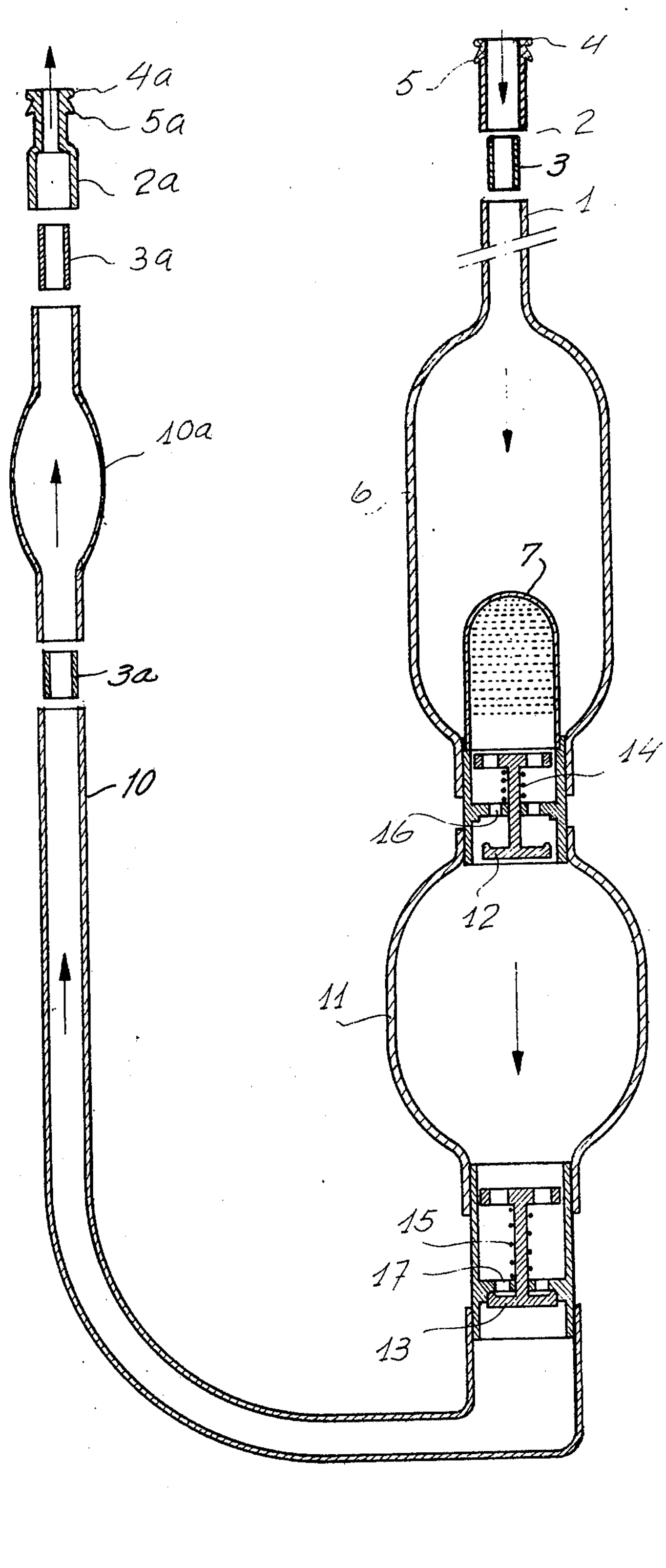
FIG. 2 is a sectional elevation of another embodiment of a device according to the invention with part of the structure of FIG. 2 shown in an exploded, disassembled condition.

The embodiment which is illustrated in FIG. 2 differs from that of FIG. 1 primarily in that the pump means 11 of FIG. 2 is adapted to be manually operated. For this purpose the pump means 11 takes the form of an elastic bulb which is capable of being manually compressed and which is capable of expanding when released by the operator. In this embodiment the components 1, 2, 4, 5, and 6 are substantially identical with those of FIG. 1. It will be noted that the cannula 2 and the tubular portion 1 are also interconnected by way of a substantially rigid tubular sleeve 3. However, in this embodiment there is no elbow 8. Instead there is situated at the suction inlet of the pump means 11 a one-way valve means 12 which will permit the fluid to flow only from the container means 6 of the suction tubular means through the filter 7 into the elastic bulb 11 when the latter expands. Thus, the one-way valve 12 is urged by a spring 14 to a position closing the openings 16 in a transverse wall of the valve which is surrounded by a tubular portion thereof interconnecting one end of the elastic bulb 11 with one end of the container means 6 as illustrated. The spring 14 normally maintains the valve 12 in its closed position closing the openings 16. When the bulb 11 is compressed, the valve 12 will remain closed. However, when it expands, in response to the suction created by this expansion the spring 14 yields to enable the valve 12 to open in the manner illustrated in FIG. 2, thus permitting the fluid to flow only from the container means 6 into the elastic bulb 11.

At the pressure outlet of the pump means 11 there is also a one-way valve means 13 which normally assumes the closed position shown in FIG. 2. The valve 13 when in its closed position closes the openings 17 of a transverse wall which extends across the interior of the tubular housing of the valve 13, this tubular housing communicating at one end with the pressure outlet of the pump means and at its opposite end with the elongated tubular portion 10 of the pressure tubular means which again is connected by way of a rigid sleeve 3*a* with the pressure-limiting portion 10*a* which in turn communicates through the sleeve 3*a* with the cannula 2*a* provided with the flange 4*a* and elastic lip 5*a* as provided above. As is apparent from FIG. 2, when the bulb 11 expands to create a suction which opens the valve 12, this suction acts together with the spring 15 to maintain the valve 13 closed. However, when the bulb 11 is compressed by the operator to increase the pressure in the interior of the bulb 11, the valve 12 will remain closed while this excess pressure will cause the spring 15 to yield while the valve 13 is displaced downwardly as viewed in FIG. 2 away from its closed position, thus permitting the fluid under pressure to flow through the openings 17 into the pressure tubular means. Thus, by successively compressing and releasing the elastic bulb 11 it is possible for the operator to provide the closed-circuit circulation of the disinfecting and possibly therapeutic treating fluid which will completely clean the nasal fossae while giving the individual substantial relief and avoiding the accumulation of mucous and the formation of centers of infection.

In both of the embodiments of the invention the elastic wall portion 10*a* of the pressure tubular means enables any overpressure in the circuit to be absorbed, such overpressure being produced for example by congestion in the nasal passages. In this way it is possible to avoid the creation of undesirable overpressure in the nasal cavities. If such an overpressure tends to form the portion 10*a* expands, being deformed due to its elasticity, thus avoiding creation of excessive pressure.

It is furthermore to be noted that it is possible to provide various cannulas 2 and 2*a* of different diameters so as to be adapted to different sizes of nasal openings.

It will thus be seen that the device of the invention is extremely simple and presents no problem in connection with its operation. It can be actuated by the individual who uses the device thus enabling the individual periodically to undergo a highly efficient treatment resulting in an effective cleaning of the nasal fossae.

Of course, the structure of the invention can be made of any suitable materials having any desired shapes and dimensions with any accessory details which do not affect the essence of the invention.

The device of the invention may be used only once and then discarded. However, it is also possible to use the device repeatedly with the device being disassembled, cleaned, and then reassembled prior to each use.

What is claimed is:

1. In a device for circulating a treating fluid through the nasal fossae, pump means having separate from each other a suction inlet and pressure outlet, suction tubular means communicating with said suction inlet and pressure tubular means communicating with said pressure outlet, said pump means cooperating with said suction and pressure tubular means for creating suction in said suction tubular means and pressure in said pressure tubular means, said suction and pressure tubular means respectively having distant from said pump means end portions which respectively carry a pair of means for placing said end portions respectively in communication with the nasal fossae, so that when a treating fluid is situated in one of said tubular means, said pump mean may be operated for circulating in a closed circuit in only one direction the treating fluid through the nasal fossae with the treating fluid entering under pressure from said pressure tubular means into one nasal fossa and being withdrawn through the other nasal fossa while entering from the latter into the suction tubular means to again be delivered by said pump means to said pressure tubular means.

2. The combination of claim 1 and wherein said pressure tubular means carries a pressure-limiting means for limiting the pressure created in said pressure tubular means.

3. The combination of claim 1 and wherein said suction tubular means includes as a part thereof a container means for containing a treating fluid to be circulated through the nasal fossae.

4. The combination of claim 3 and wherein a filter means is situated in said suction tubular means between said container means and said suction inlet of said pump means for filtering fluid withdrawn from said container means.

5. The combination of claim 2 and wherein said pressure-limiting means forms part of said pressure tubular means and includes a portion of said pressure tubular means which is made of an elastic, deformable wall which responds to pressure greater than a given limiting pressure for expanding and increasing the volume of said pressure tubular means at the location of said pressure limiting means for preventing an excessive increase in pressure.

6. The combination of claim 1 and wherein said pump means is a motor-driven pump means.

7. The combination of claim 1 and wherein said pump means is a manually operable pump means.

8. The combination of claim 7 and wherein said manually operable pump means includes an elastic bulb adapted to be manually compressed and a pair of one-way valve means respectively situated at said suction inlet and pressure outlet for providing for flow of fluid only from said suction tubular means into said elastic bulb during expansion of the latter and for flow of fluid only out of said elastic bulb into said pressure tubular means during manual compression of said elastic bulb.

9. The combination of claim 1 and wherein each means at each end portion of each tubular means for placing the latter in communication with a nasal fossa includes a cannula carrying at its exterior an elastic flexible sealing flange surrounding each cannula for placing the latter in communication with a nasal fossa in a substantially fluid-tight manner.

10. The combination of claim 4 and wherein said pressure tubular means has an elastic deformable wall portion adapted to expand in response to excessive pressure for limiting the extent to which pressure can build in said pressure tubular means.

* * * * *